(12) United States Patent
Arnold

(10) Patent No.: US 8,186,880 B1
(45) Date of Patent: May 29, 2012

(54) EXTENDED AND FIXED INTABLE SIMULTANEOUSLY IMAGED CALIBRATION AND CORRECTION METHODS AND REFERENCES FOR 3-D IMAGING DEVICES

(76) Inventor: Ben A. Arnold, Columbia, KY (US)

( * ) Notice: Subject to any disclaimer, the term of this patent is extended or adjusted under 35 U.S.C. 154(b) by 0 days.

(21) Appl. No.: 12/626,610

(22) Filed: Nov. 25, 2009

Related U.S. Application Data

(60) Provisional application No. 61/118,438, filed on Nov. 27, 2008.

(51) Int. Cl.
G01D 18/00 (2006.01)
(52) U.S. Cl. .......................... 378/207; 378/18
(58) Field of Classification Search .......... 378/18, 378/207
See application file for complete search history.

(56) References Cited

U.S. PATENT DOCUMENTS

| | | | | |
|---|---|---|---|---|
| 4,233,507 A | * | 11/1980 | Volz | 378/18 |
| 4,649,561 A | * | 3/1987 | Arnold | 378/207 |
| 4,663,772 A | * | 5/1987 | Mattson et al. | 378/18 |
| 4,724,110 A | | 2/1988 | Arnold | |
| 4,782,502 A | * | 11/1988 | Schulz | 378/18 |
| 4,870,666 A | * | 9/1989 | Lonn | 378/18 |
| 4,922,915 A | | 5/1990 | Arnold et al. | |
| 4,985,906 A | * | 1/1991 | Arnold | 378/18 |
| 5,034,969 A | | 7/1991 | Ozaki | |
| 5,068,788 A | | 11/1991 | Goodenough et al. | |
| 5,222,021 A | * | 6/1993 | Feldman et al. | 378/18 |
| 5,235,628 A | * | 8/1993 | Kalender | 378/207 |
| 5,335,260 A | | 8/1994 | Arnold | |
| 5,442,674 A | * | 8/1995 | Picard et al. | 378/20 |
| 5,521,955 A | * | 5/1996 | Gohno et al. | 378/18 |
| 5,577,089 A | | 11/1996 | Mazess | |
| 5,696,805 A | | 12/1997 | Gaborski et al. | |
| 5,712,892 A | | 1/1998 | Weil et al. | |
| 5,757,877 A | | 5/1998 | Wilting | |
| 5,774,519 A | * | 6/1998 | Lindstrom et al. | 378/18 |
| 5,782,762 A | | 7/1998 | Vining | |
| 5,891,030 A | | 4/1999 | Johnson et al. | |
| 6,026,142 A | | 2/2000 | Gueziec et al. | |
| 6,226,350 B1 | | 5/2001 | Hsieh | |
| 6,233,304 B1 | | 5/2001 | Hu et al. | |
| 6,243,437 B1 | | 6/2001 | Hu et al. | |

(Continued)

OTHER PUBLICATIONS

Kolta et al., Three-dimensional X-ray absorptiometry (3D-XA): a method for reconstruction of human bones using a dual X-ray absorptiometry device, Osteoporos Int, 2005, 16, pp. 969-976.*

(Continued)

Primary Examiner — Alexander H Taningco
(74) Attorney, Agent, or Firm — Jerry Turner Sewell

(57) ABSTRACT

Calibration and reference samples with reduced cross-sectional areas encased within imaging tables or couch pads have low attenuation properties and provide patient comfort. The samples are stable and provide reproducible images without artifacts. The torso-length samples avoid positioning errors and misalignment. Sample density or mass calibration materials include calcium compounds representative of bone and calcifications, iodine compounds for contrast angiography, gadolinium compounds for MRI, and fat and tissue equivalent materials. Density corrections for variable patient scatter and imperfect image reconstructions improve quantitative measurement. Automated computer methods detect the samples and record readings on all images over the extent of the scans without operator interaction. Spatial references function as location references and enable spatial correction of device imperfections such as point spread function (PSF) or motion for improved images. Comparative analysis of backward and forward projections corrects images based on simultaneous imaging of the references of known properties.

15 Claims, 17 Drawing Sheets

U.S. PATENT DOCUMENTS

| | | | |
|---|---|---|---|
| 6,278,761 | B1 | 8/2001 | Kim et al. |
| 6,302,582 | B1* | 10/2001 | Nord et al. .................... 378/207 |
| 6,320,931 | B1* | 11/2001 | Arnold ............................ 378/56 |
| 6,421,552 | B1 | 7/2002 | Hsieh |
| 6,639,965 | B1 | 10/2003 | Hsieh et al. |
| 6,674,834 | B1 | 1/2004 | Acharya et al. |
| 6,697,451 | B2 | 2/2004 | Acharya et al. |
| 6,789,943 | B2* | 9/2004 | Zapalac ........................ 378/207 |
| 6,990,222 | B2 | 1/2006 | Arnold |
| 7,127,096 | B2 | 10/2006 | Kaufman et al. |
| 7,251,306 | B2* | 7/2007 | Sauer et al. ........................ 378/4 |
| 7,409,035 | B2* | 8/2008 | Kaufman et al. ............... 378/18 |
| 7,471,765 | B2* | 12/2008 | Jaffray et al. .................. 378/65 |
| 7,583,778 | B2* | 9/2009 | Mori ................................ 378/4 |
| 2003/0048867 | A1* | 3/2003 | Acharya et al. ................ 378/18 |
| 2003/0095693 | A1* | 5/2003 | Kaufman et al. ............. 382/128 |

OTHER PUBLICATIONS

Kolta et al., In vivo 3D reconstruction of human vertebrae with the three-dimensional X-ray absorptiometry, Osteoporos Int, 2008, 19, pp. 185-192.*

Agatston, Arthur S. et al. Quantification of coronary artery calcium using ultrafast computed tomography, American College of Cardiology, 1990; 15: pp. 827-832.

Baldy, R.E. et al., A Fully-Automated Computer Assisted Method of CT Brain Scan Analysis for the Measurement of Cerbrospinal Fluid Spaces and Brain Absorption Density, Neuroradiology, vol. 28, 1986, pp. 109-117.

Brown, Matthew S. et al., Knowledge-based segmentation of thoracic computed tomography images for assessment of split lung function, Medical Physics, vol. 27, No. 3, Mar. 2000, pp. 592-598.

Grashuis, J.L. et al., Semi-Automatic Contour Detection in CT-Scans of the Lumbar Spine, Proceedings of the Sixth International Workshop on Bone and Soft Tissue Densitometry, Buxton, England, Sep. 22-25, 1987, p. 33.

Greaser, L.E. 3rd et al., Electron-beam CT: the effect of using a correction function on coronary artery calcium quantitation, Acad. Radiol., vol. 6, No. 1, Jan. 1999, pp. 40-48. (one-page abstract).

Heil, Robert H., Jr., et al., Quantitative Materials Evaluation and Inspection with the Image Analysing Computer, Proceedings of the Society of Photo-Optical Instrumentation Engineers, Feb. 1972, pp. 131-143.

Kachelreiss, Marc et al., ECG-correlated image reconstruction from subsecond multi-slice spiral CT scans of the heart, American Institute of Medical Physics, vol. 27, No. 8, Aug. 2000, pp. 1881-1902.

Kalender, Willi A. et al., Vertebral Bone Mineral Analysis: An Integrated Approach with CT, Radiology, 1987, vol. 164, No. 2, Aug. 1987. pp. 419-423.

Kalender, W.A. et al., Methodological Aspects of Bone Mineral Measurements by QCT: Minimizing Operator Influence on Reproductibility, Proceedings of the Sixth International Workshop on bone and Soft Tissue Densitometry, Buxton, England, Sep. 22-25, 1987, p. 31.

Keller, James M. et al., Automatic Outlining of Regions on CT Scans, Journal of Computer Assisted Tomography, vol. 5, No. 2, Apr. 1981, pp. 240-245.

Kemerink, G.J. et al., Scanner conformity in CT densitometry of the lungs, Radiology, vol. 197, No. 3, Dec. 1995, pp. 749-752. (one-page abstract).

McCullough, Cynthia H., Ph.D., Electron-Beam CT: Use of a Calibration Phantom to Reduce Variability in Calcium Quntitation, Departments of Diagnostic Radiology and Physiology and Biophysics, Mayo Clinic and Mayo Foundation, Rochester, Minnesota, vol. 196, No. 1, Jul. 1995, pp. 159-165.

Reed, Judd E. et al., System for Quantitative Analysis of Coronary Calcification via Electron Beam Computed Tomography, Medical Imaging 1994, Physiological and Function from Multidimensional Images, SPIE, vol. 2168, Feb. 13-14, 1994, pp. 43-53.

Stoel, B.C. et al., Sources of error in lung densitometry with CT, Invest. Radiol., vol. 34, No. 4, Apr. 1999, pp. 303-309. (one-page abstract).

Wankling, P.F. et al., Computer Recognition Applied to C.T. Scans for the Automation of the Procedure for Bone Mineral Measurement Allowing Consistent Measurement Without Operator Intervention, Proceedings of the Sixth International Workshop on Bone and Soft Tissue Densitometry, Buxton, England, Sep. 22-25, 1987, p. 32.

Yoon, H. C. et al., Coronary artery calcium: alternate methods for accurate and reproducible quantitation, Acad. Radiol., vol. 4, No. 10, Oct. 1997, pp. 666-673. (one-page abstract).

General Electric, Marketing Materials distributed in 1987, four pages.

Technical Note, Automatic Outlining Technique for EMI Scanner Pictures, Medical & Biological Engineering & Computing, vol. 17, Sep. 1979, pp. 693-694.

* cited by examiner

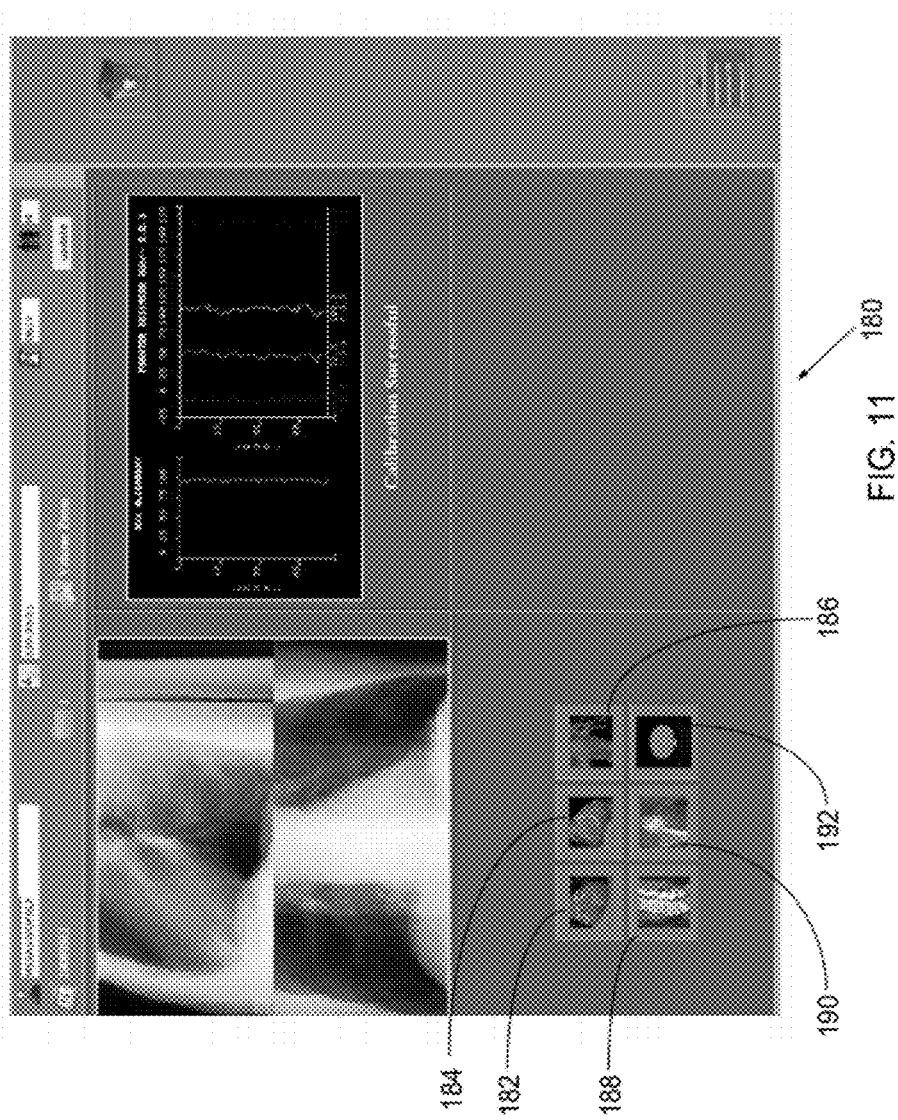

EXTENDED AND FIXED INTABLE SIMULTANEOUSLY IMAGED CALIBRATION AND CORRECTION METHODS AND REFERENCES FOR 3-D IMAGING DEVICES

RELATED APPLICATIONS

The present application claims the benefit of priority under 35 USC §119(e) to U.S. Provisional Application No. 61/118,438, filed on Nov. 27, 2008.

BACKGROUND OF THE INVENTION

1. Field of the Invention

The disclosure in the present application is in the field of 3-D volumetric medical imaging, and, in particular, is directed to an improved device and method to determine tissue properties in the body of a subject.

2. Description of the Related Art

Many diagnostic 3-D imaging devices are used in modem medicine for many types of exams, which are performed by subjective viewing of the images on either film or more commonly on electronic displays. This subjective viewing uses assumed quantitative image pixels, which define boundaries of tissues, organs or foreign masses, and discrimination of tissue types based on grey scale or color images, representative of the underlying tissue properties. Identification of diagnostic details is fundamentally dependent upon the detection of image detail edges. Diagnostic interpretation or measurements from these images assume an appropriate relationship of the image to the tissue property. All of these imaging devices however have significant limitations for quantitative measurements because the relationship is not sufficiently accurate or defined. The embodiments disclosed in the present application are directed at improving these limitations while reducing costs, time and effort in the clinical setting.

Measurement, display, and analysis of tissue properties from medical images have many diagnostic benefits in the living subject. These include such measures as density, mass, volume, edges, etc.; image display reference values, translucency, texture; tissue water or hydrogen content, electron density, blood vessel iodine contrast media concentration and density or blood flow, tissue iron content, fat/muscle ratio, air/tissue ratio, and the like. Modern imaging devices enable the potential to identify and quantify, either automatically or manually, most organs and tissues of the body. The imaging devices to which the improvements disclosed herein are directed provide a set of volumetric images acquired from multiple projection angles, which allow reconstruction of images in various planes. Such devices include dual-energy and single-energy CT scanners, rotational C-arms, MRI devices, x-ray tomosynthesis and 3D DXA (dual-energy X-absorptometry) in which the x-ray source is moved to provide various projections, such as a Hologic 3-D DXA device in development. Several tissue measurements of interest include bone density, lung nodule density, cardiac, aortic and vascular calcifications, vascular soft plaque, fat measurements, muscle mass, lung volume and density (emphysema and the like), liver iron content, perfusion and blood flow, organ volume, density and mass, contrast angiography and the like. Tissue corrections for radiotherapy dose calculations are based on the electron density. Accurate and conveniently available measures of true tissue properties and their change with disease conditions or therapy allow diagnostic analysis of images and new diagnostic criteria not currently possible.

The methods disclosed in this application provide improved accuracy and greater ease in all of these potential applications.

Radiologists routinely make subjective and even quantitative measurements of foreign masses, tissues or organs by manually placing cursors to define the 2-D extent of the target. If the window and/or level (brightness and contrast) are changed in the display, the apparent size of the target changes because the boundary is not discrete and is moved in or out of the display range. Thus, the measured object size is frequently inaccurate and will vary from operator to operator and from scanner to scanner depending on the display conditions and scanner properties. In addition, the process to set and adjust the window and level requires operator time and is currently very inefficient. Electronic image data are frequently erased, and only the films retained for the medical records.

Prior art methods have allowed CT scanners to be used as quantitative instruments for bone density measurements in quantitative computerized tomography (QCT) by the use of calibration phantoms scanned simultaneously with the patient (simultaneous calibration). Such phantoms have greatly aided the standardization accuracy and reproducibility of bone density measurements. Representative prior art methods have been disclosed in U.S. Pat. No. 4,233,507 to Volz), U.S. Pat. No. 4,985,906 to Arnold, U.S. Pat. No. 5,335,260 to Arnold, U.S. Pat. No. 4,782,502 to Schulz, U.S. Pat. No. 4,651,335 to Kalender, U.S. Pat. No. 4,870,666 to Lonn, and others. These prior phantom designs included, for example, samples within pillows and positioned beside the subject; a flexible phantom positioned on top of the subject; a flexible phantom positioned under the subject with means to force contact to patient; samples within a slot between two couch pads; and in a removable, rigid structure or table top section in the original Volz patent.

The Volz patent used samples with 5 cm cross-sectional diameters and subsequent improvement patents used similar or larger sample areas because of the need to have sufficient numbers of pixels in each CT slice region of interest (ROI) for statistical measurements. The base material and calibration samples were large and dense and increased the dose and image artifacts. U.S. Pat. No. 4,985,906 to Arnold discloses improvements to prior phantoms by using tissue equivalent base material with reduced size and mass to minimize beam hardening effects.

In U.S. Pat. No. 6,990,222 to Arnold discloses a method for hybrid calibration using simultaneous phantom calibration along with internal tissue references of the individual patient. U.S. Pat. No. 6,990,222 is incorporated by reference herein in its entirety. More recently, fast multi-detector MDCT scanners have been used for coronary and aortic calcium analysis with or without simultaneous phantom calibration.

The prior calibration methods were successful because CT numbers, (Hounsfield Units, HU), are only estimates of the x-ray attenuation coefficients of tissue relative to water as the manufacturer's calibration reference material. CT numbers fail to be truly quantitative for several reasons. For example, the tissue attenuation coefficients are photon energy dependent, and the x-ray beam energy spectra are not measured or known for individual patients. Further, many beam energy spectra exist in each CT slice (e.g., a unique spectrum for each path length through the patient and seen at a particular detector element, and a unique spectrum for each view through the patient). The beam spectrum changes with the thickness and composition of tissues in the path length. The quantities of fat, soft tissue, air, and bone vary with each projection. X-ray tube filtration to shape the beam intensity also changes the beam spectrum resulting in variations in tissue attenuation based on locations within the field of view. Scattered radiation is also variable and dependent on some of these parameters. Manufacturers' calibrations (for example, CT number and beam hardening corrections in current practice and scatter correction) are based on idealized phantoms scanned independently from the patient, which are often circular in shape and composed of water, plastics, or other homogeneous, synthetic materials. These differ significantly from the shape and varied composition of real patients. Image pixel intensities vary from image to image, and are dependent on table height, position in the beam, scanner drift, tube changes, manufacture reconstruction software, body region thickness and volume, field of view, and sometimes even the time of day as the imagers warm up.

Measurement errors also result from organ motion artifacts, tissue heterogeneity (fat, muscle, blood mixtures in sub-voxel volumes), gantry wobble and vibrations of the x-ray source, escape of K x-rays in the detectors, reconstruction algorithm, electronic noise, local beam hardening, scattered radiation and structure artifacts (usually from the presence of larger bones, air volumes and table structures). As a result of the measurement errors, tissue densities vary with imaging device, image acquisition parameters, gating and motion, etc., some of which have been reported. In addition, measurements will vary with patient size and body type which is poorly recognized. Because of the finite detector element size, the x-ray tube focal spot size and geometry, source movement during scanning and image back projection reconstruction imperfections, the finite number of views and source and/or table movement, the reconstruction of objects is not exact resulting in edge blurring by the point spread function (PSF) and loss of accurate tissue density representations at edges of objects. As a result, bone density and calcium scores vary significantly with different devices, over time and between different institutions, patient body composition and imaging techniques. The above-referenced measurements are also dependent on this listing of sources of errors.

Prior methods for simultaneous CT calibrations in bone density measurements have used calcium phantoms which are removed after each exam. This requires the operator to place the phantom on the CT table before and to remove the phantom after each quantitative study and then place the phantom in storage. Further, the operator is required to position the phantom in a surrounding foam pad for patient comfort and then to position the phantom and pad and patient in the CT field-of-view (FOV). It is important to reproduce the position of the phantom in the FOV and to avoid its movement during the scans. Misalignments cause variable results and failure to reproduce positioning on follow-up exams months or years later can reduce measurement precision. Unlike these prior methods, the device and methods disclosed in the present application overcomes all of these limitations. Further, the operator does not need to be concerned with phantom positioning or repositioning and thus saves time during each patient procedure.

With prior methods, any study without the phantom cannot then or later be analyzed. With the device and method disclosed herein, any prior study from months to years can be analyzed at any later date since the references may always be present in all images and all studies. Increased radiation doses, costs, times and efforts of repeating scans for quantitative analysis are avoided when existing scans made for other exams can be reprocessed. Since many medical conditions such as osteoporosis, coronary or vascular disease, emphysema, body composition, etc., are chronic and slowly changing conditions, later measurements are likely to remain highly relevant even if analyzed months or years later.

Prior art methods employ large cross-sectional area phantoms with higher density base materials. The large sample sizes were required because software methods operated on usually 2 to 4 reconstructed thick slices by manual or later automated methods. (See, for example, U.S. Pat. No. 4,922,915 to Arnold.) These features are now known to cause beam hardening and scatter artifacts and cause streaks from the reference phantom itself. The larger/dense phantom increases radiation dose to the patient and/or reduces image quality by adding noise and scatter. Because of the automated software methods disclosed herein, much smaller, cross-sectional reference samples can be used with great advantage.

Prior methods and phantoms create patient discomfort from the hard material and sharp edges as well as large size. Patient discomfort often leads to patient motion during the scan creating additional errors. The device and method disclosed herein overcome patient discomfort. Automated software methods to locate and measure reproducibly the very small diameter samples were not available in prior methods. Further, finding and measuring these small samples which are now not rigid and which extend over long distances required advanced methods disclosed herein. With the advent of MDCT scanners with several hundred CT images per exam, calibration on all images in background automatically was required.

Prior methods used phantoms of reduced length, which were significantly shorter than the length of the patient's torso. The required large sample sizes and removal of the phantom between studies resulted in short phantoms. The phantom had to be repositioned between multiple scans, such as hip and thoracic vertebral BMD scans. In addition, the operator must be aware of the position of the phantom and/or scout scan the patient to verify phantom positioning under the anatomical region to be scanned. This requires added time and radiation dose to the patient. The disclosed devices and method overcome these limitations.

Prior methods have been limited primarily to bone density measurements using calcium equivalent phantom samples. Additional reference and calibration materials and new calibrations and image corrections are possible with the currently disclosure method and system.

Prior methods to correct CT scanners for gantry, tube and table motion and methods to measure or correct for image reconstruction, detector variations, system motion and wobble, have used phantoms with pins, spheres and small diameter wires contained within idealized phantoms. These phantoms and test objects have been scanned independent of the patients. These methods, while providing the ability to correct for scanner imperfections in idealized conditions, are not necessarily representative of the imaging device when the patients are present and are not representative of the device at the time of specific clinical exams. X-ray imagers and CT scanners are known to drift, change sensitivity with use and environmental conditions, patient size and weight, (CT table movement, backlash and bending), and scanner and scanning parameters. For all of these and additional reasons, current test phantoms and methods for image corrections have limitations because they have been applied without the patient present. The disclosed device and methods by including similar phantom targets for image corrections simultaneously with each individual patient exam and at the relevant time of the exam overcomes many of these limitations.

SUMMARY OF THE INVENTION

An aspect in accordance with the invention disclosed herein is a calibration and reference couch pad, patient support device or tabletop that contains a variety of reference sample materials and test targets. The samples and targets are permanently enclosed within the pad, device or tabletop at fixed locations and are scanned simultaneously with patient scans. The samples and targets are small in cross-sectional size and area which provides patient comfort minimizes patient movement and avoids image artifacts. The samples and targets are further manufactured with high reproducibility and homogeneity and of sufficient length or repeating placements to always be present in the image for all torso exams without operator effort or placement or alignment verification. Any scan on any body part and at any time can be post-analyzed for a variety of tissue and image quality measurements. Patient comfort and radiation dose are improved. Operator time and effort is reduced. Costs to patients or facilities for repeat or additional scans at a later date are also reduced.

One aspect of the disclosure is advanced software methods to identify and measure the very small size calibration samples and to do so over extended sample lengths. The samples being of a smaller cross-sectional area and extended length tend to move and flex with patient weight. The automated software methods were required to operate in background without operate assistance and to reproducible identify, center measurement regions and apply the corrections and calibrations in acceptable times on large image sets.

Additional reference samples and test targets facilitate new and innovative analysis, corrections and calibrations for a variety of clinical exams or scanner imperfections. Calibration of in vivo iodine contrast distribution and blood flow can be achieved with simultaneous calibration for the first time. Dual-energy CT or 3-D DXA can be corrected for imperfect energy subtraction and associated algorithms for such purposes as CT angiography, bone removal or tissue type separations. Bone density and vascular calcifications can be calibrated for any region of the body and without patient or phantom repositioning and without operator concern for alignments during the scans.

Image reconstruction imperfections can be analyzed and corrected which are representative of the actual patient and scan of interest. Image quality, motion errors, image blur from the system represented by the device PS, table, gantry and X-ray source motion and backlash can be determined and corrected and under the specific conditions of the scans to improve image quality and quantitative measurements.

Other aspects of the disclosed embodiments are improved calibration and reference devices and methods which allow improvements in current 3-D x-ray exams as well as development of new quantitative exams. In addition, improved references and methods for corrections of device imperfections are disclosed which are device, technique, patient and time specific.

Prior to the disclosure herein, uses of simultaneous calibration phantoms or methods for measurements of soft tissue density, non-calcified vascular plaque (so-called soft plaque), CT angiography, lung density, dimensional measurements or correction of image imperfections were not known. It is desirable to provide improved calibration methods for all the tissues of the body.

BRIEF DESCRIPTION OF THE DRAWINGS

Without limiting the scope of the invention, the foregoing aspects and other aspects in accordance with embodiments disclosed herein are described herein in connection with the accompanying drawings, images, and figures in which:

FIGS. 5A and 5B illustrate an axial CT image of the abdominal region of a patient with a representative calibration device under the patient, wherein FIG. 5A is displayed at a relatively common window/level setting, and FIG. 5B is a insert windowed to a low level and high contrast to show the position of the pad within the CT table;

FIGS. 6A, 6B and 6C illustrate scans of the pad with an iodine reference, wherein FIG. 6A is a scan of a patient with the iodine reference, FIG. 6B is a scan of a simple QA test phantom, and FIG. 6C is a windowed scan of the pad and the CT table that shows the absence of artifacts with the iodine sample;

FIG. 11 illustrates an application selection screen from the automated software showing Icons for six calibrated, quantitative application programs, which is exemplary of the software program opening screen after exam selection, which use Icons instead of language throughout the program.

DETAILED DESCRIPTION OF THE PREFERRED EMBODIMENT

An important determination of the present disclosure is that the energy X-ray attenuation response (slope of the regression calibration equation) can be measured independently from the intercept of the regression calibration equation (i.e., the bias component). An additional determination of this discloser is that the slope is relatively independent of the sample size and surrounding material. The hybrid calibration method in combination with the disclosed device and methods has been shown to be superior to the use of external phantoms only and particularly so when large and dense phantoms are used.

Another important determination of the present disclosure is that Z-axis integration of pixels in the small cross-sectional samples can be used preferably to phantoms with large samples and single slices. Practical use of the presently disclosed device incorporates innovative software methods which automatically detect and measure the small samples, which also may move somewhat from scan to scan. Prior methods measure bone density on single reconstructed CT slices, typically using 2 to 5 slices for each session. The slices were 8-10 mm thick and were positioned or reconstructed through 2 to 5 individual vertebrae. Locating and positioning regions-of-interest (ROI) measurement areas within the larger phantom samples required much less complex software methods. The ROIs could be manually adjusted in practical times, and allowed much slower run times or real time operation with operator present.

Innovative and advanced software methods are used to detect and measure the small samples of the disclosed system without operator assistance and running in background mode. The software methods automatically locate and determine measurement regions within each sample and on every CT slice. CT studies containing hundreds of axial images and even greater than 1,000 images can readily be analyzed without operator interaction. The automated software ("The Phantom Finder") operates in background mode and can archive region placements on hundreds of images in a few seconds (e.g., on the order of 5 seconds). The auto Phantom Finder is particularly advantageous for small calibration and test samples, for high resolution (small voxel, thin CT slices and/or smaller pixels) images and volumetric scans of large body regions or whole body scans. The software allows variable Z-axis integration, which can be adapted to different scan parameters, different patient size and body mass and resulting beam hardening, scatter and image noise effects.

Figure 1:
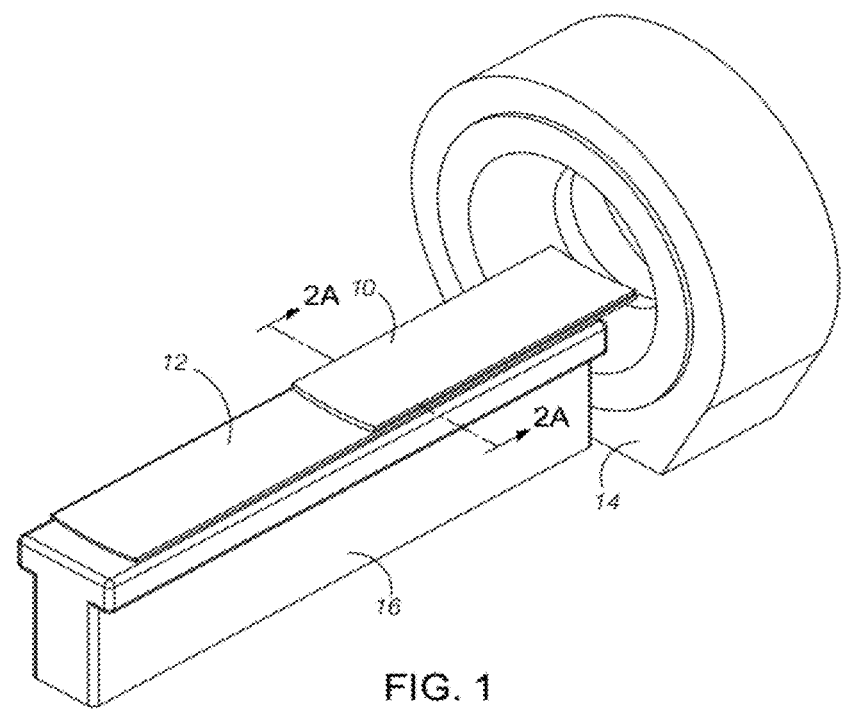
FIG. 1 illustrates a partial perspective view of an embodiment of a calibration couch pad on a scanning table proximate to the tunnel of a CT scanner.
Figure 2A:
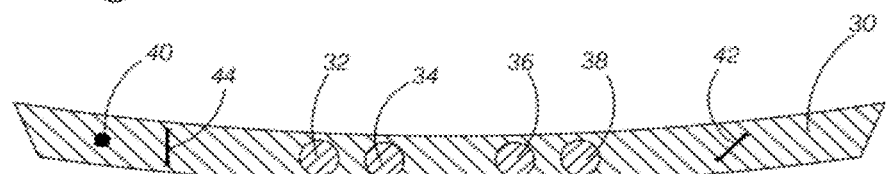
FIG. 2A illustrates a schematic drawing of a cross section of the calibration couch pad of FIG. 1 taken along the section line 2A-2A in FIG. 1, which illustrates test targets and calibration samples.

A representative embodiment of the improved full-torso phantom is shown in FIG. 1, which illustrates a calibration pad 10 positioned on a CT scanner table 12 proximate to the scanning portal of a CT scanner 14 (represented pictorially). The scanner table rests on a support platform 16. The pad replaces the customary and usual couch pad of imaging devices and remains in place for all exams without removal. FIG. 2A illustrates a cross section of the calibration pad of FIG. 1 taken along the section line 2A-2A in FIG. 1. One skilled in the art will appreciate that during an imaging procedure, a subject (not shown) is placed on the scanner table. The scanner table moves longitudinally with respect to the top of the support platform to move the support pad and the subject into the portal of the CT scanner. Accordingly, the reference pad is scanned simultaneously with the subject.

Figure 3A:
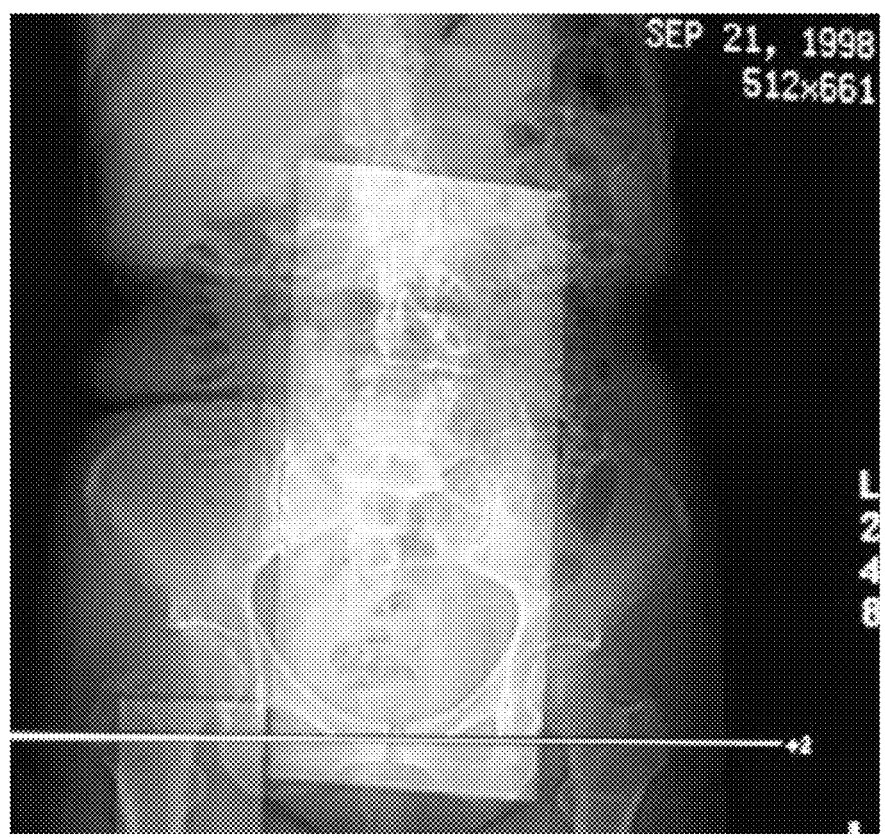
FIGS. 3A, 3B, 3C and 3D illustrate representative CT images of prior art phantoms to illustrate certain problems overcome by the embodiments disclosed herein.
Figure 3B:
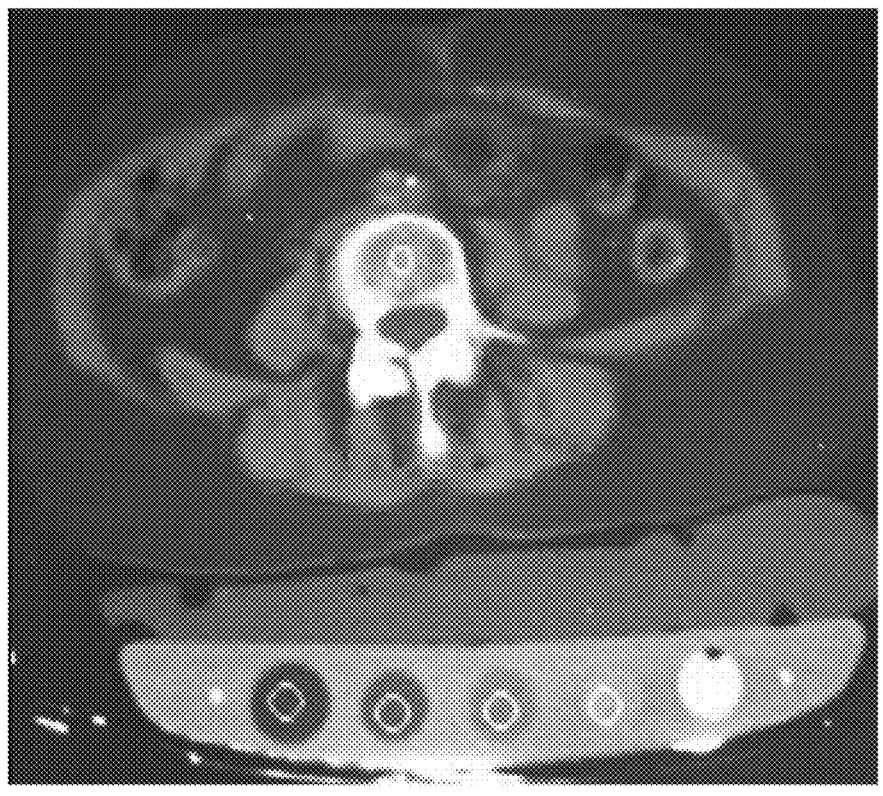
Figure 3C:
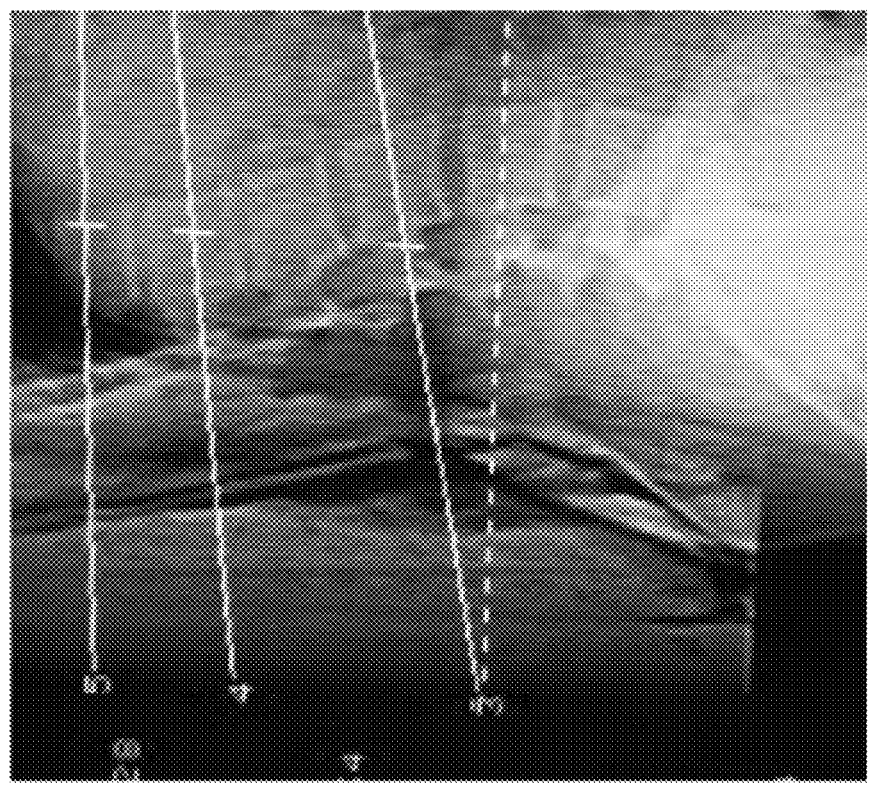
Figure 3D:
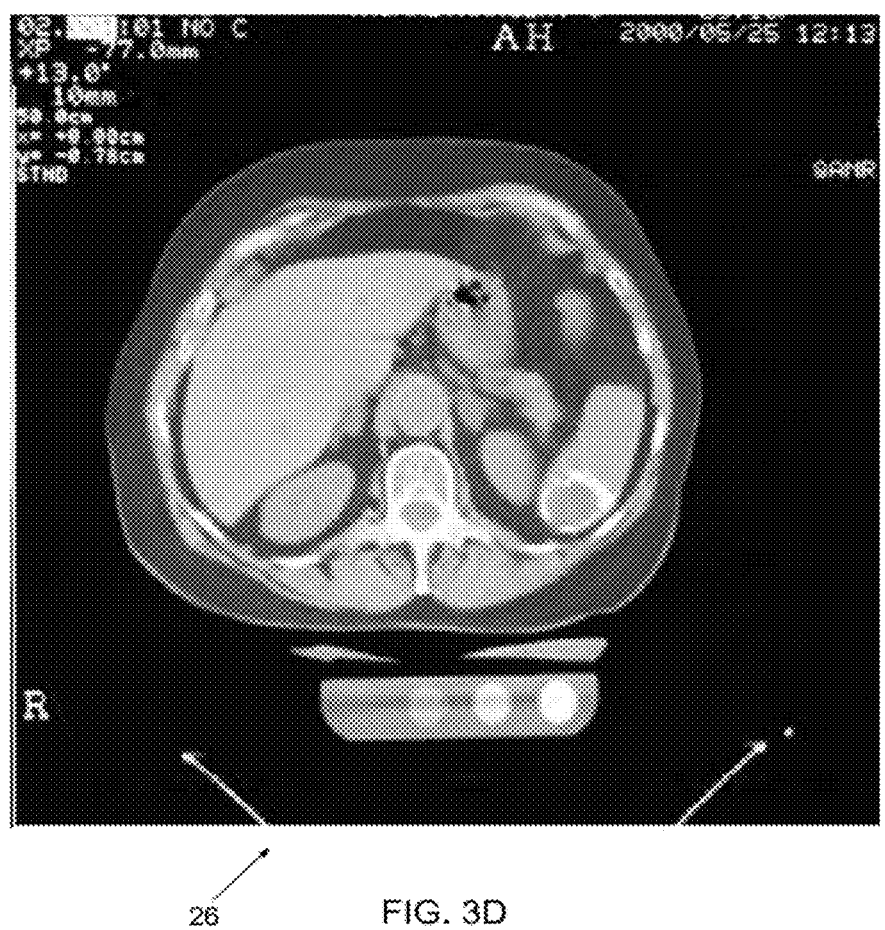

FIGS. 3A, 3B, 3C and 3D illustrate CT images of examples of prior phantoms and the associated artifacts, streaks, miss positioning and discomfort of the sharp edges of larger phantoms. FIG. 3A illustrates an image 20 that shows an angular mispositioning of a larger prior phantom. FIG. 3B illustrates an image 22 that shows the large size of prior art phantoms as well as the large diameters of the samples. The high density of the phantom base material (lighter) is apparent compared to the density of the patient tissues (fat and muscle are both darker). FIG. 3C illustrates an image 24 that shows an example of a sharp edges pushing into the back of the patient during the scan. FIG. 3D illustrates an image 26 of an improved prior art phantom that still includes streak artifacts and scatter effects.

As illustrated in FIG. 2A, the calibration pad 10 comprises a material 20, such as, for example, a foam pad. In the illustrated embodiment, the pad has a width of approximately 16 inches (41 cm) and a thickness of approximately 1.1 inch (2.8 cm). Preferably, the calibration pad extends for at least the full length of the subject's torso. In one embodiment, the length of the calibration pad is approximately 50 inches (127 cm). The calibration pad includes a plurality of reference samples (e.g., 4 reference samples in the illustrated embodiment). Each reference sample has a small diameter of approximately 0.6 inch (1.5 cm) and extends for the length of the calibration pad. The reference samples have known densities and produce ROI mean CT numbers ($HU_s$) for each sample. For example, a first reference sample 32 may preferably contain water density or 0 concentration of the calibration additive material. The calibration additive material is advantageously a calcium-containing material such as calcium hydroxyapatite (CaHA) or a stable iodine compound (for example, hydriodic acid or sodium iodine from Ajay North America, Powder Springs, Ga.) in a solid water equivalent synthetic material. In the illustrated embodiment, a second reference sample 34 and a third reference sample 36 comprise calcium hydroxyapatite. For example, the second CaHA reference sample has a density of 75 mg/cc, and the third CaHA reference sample has a density of 150 mg/cc. A fourth reference sample 38 may comprise a material having the density of fat or a sample having a concentration of iodine (e.g., 100 mg/cc of iodine). Alternative reference samples may comprise varying concentrations of iodine. For example, the four reference samples may comprise a sample of 0 mg/cc of iodine, a sample of 100 mg/cc of iodine, a sample of 200 mg/cc of iodine, and a sample having the density of fat. Although only four reference samples are shown in the illustrated embodiment, additional reference samples (e.g., a total of 5 reference samples may be included). As discussed below, the reference samples have characteristics that do not degrade the images for diagnosis when imaged simultaneously with the subject.

In certain preferred embodiments, the calibration pad 10 further includes a wire 40 (e.g., a small diameter aluminum wire) that extends for the full length of the calibration pad. In certain preferred embodiments, the calibration pad further includes a metallic or increased density material in the form of a ribbon (or sheet) 42 that extends for the full length of the pad. In certain preferred embodiments, the calibration pad further includes a plurality of metallic pins 44 (one shown in FIG. 2A) repeated at known distances. In certain preferred embodiments, the metallic pins are advantageously positioned at multiple angular orientations including vertical, lateral with reference to the image plane, and the like. Correction inserts may include microspheres of CaHA or aluminum (preferably having diameters smaller than the PSF of the imaging device). These microspheres may preferably be distributed in repeated locations along the length of the reference device. Such particles may also comprise short length, small diameter wires or calcium compounds. These inserts may also be blended into the larger reference inserts such as preferably the zero concentration sample. This may be achieved by blending and then extruding the blended mixture to form the insert.

Figure 2B:
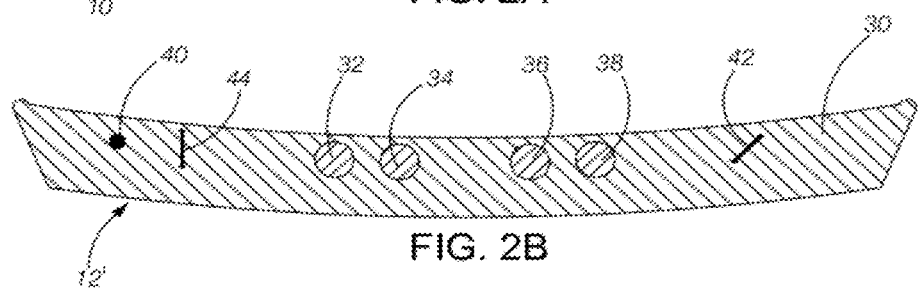
FIG. 2B illustrates a schematic drawing of a cross-section of an alternate embodiment of a calibration reference structure in which the test targets and the calibration samples are encased directly into the scanning table.

In an alternative embodiment shown in cross section in FIG. 2B, the reference samples 32, 34, 36 and 38 and other inserts 40, 42 and 44 are encapsulated directly into a modified scanner table 12'. For example, the modified scanner table advantageously comprises carbon fiber or other suitable material.

Figure 4A:
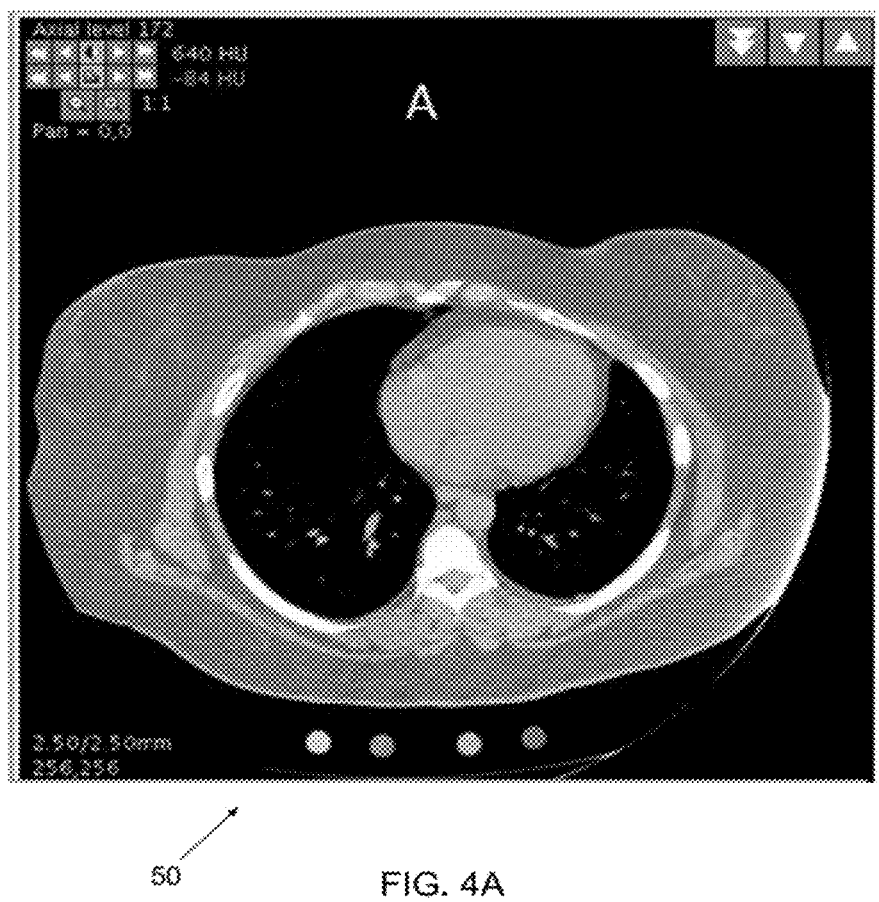
FIGS. 4A, 4B and 4C illustrate CT images of a patient scan of the chest area with the calibration and test pad in place in the upper left (image 4A), wherein the lower left image (image 4B) has been windowed down to a low level and contrast to show that no artifacts or image streaks are created from the small samples and low density pad material, and wherein the right Image (image 4C) is a coronal reformation of the scan showing 4 reference samples extending over a length of 50 inches (127 cm)
Figure 4B:
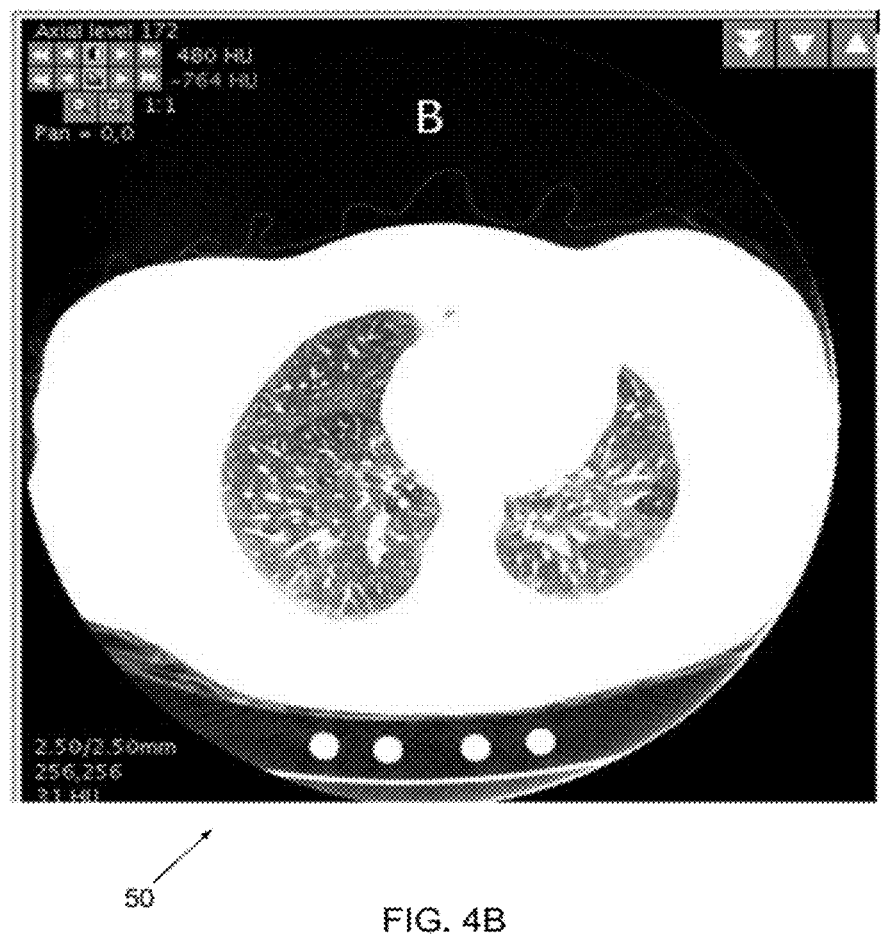
Figure 4C:
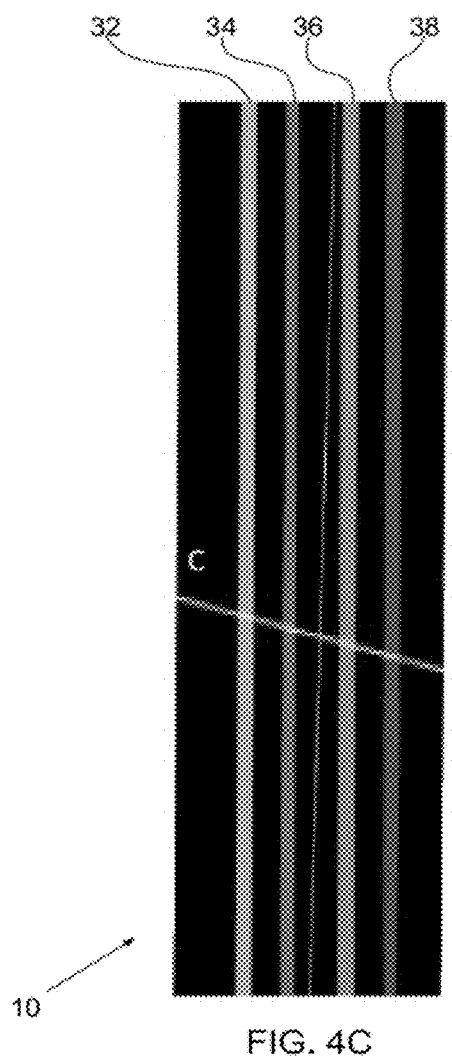

Using the calibration pad 10 of FIGS. 1 and 2A (or the alternative modified scanner table 12' of FIG. 2B), a CT scan of the subject is first taken with the subject lying on the reference calibration pad. Several CT images are taken in a short time period. Preferably, CT images are taken using a multi-slice spiral scan CT scanner (represented by the CT scanner 14 in FIG. 1), although any CT scanner can be used for many tissues. Scans of the heart for coronary calcium analysis require fast scan times to stop the motion of the beating heart but slow or fast scanners can be used. After reconstruction of the CT images in the scanner computer, a first cross-sectional image of the subject is displayed in an axial image such as the image 50 illustrated in FIG. 4A. In particular, FIG. 4A illustrates a representative image taken through the chest including the heart, lungs and chest wall with the reference pad samples under the subject. FIG. 4B illustrates the same image in FIG. 4A but with the image windowed to a higher resolution to show the detail within the lungs. Even at the higher resolution of FIG. 4B, the reference samples in the calibration pad do not introduce any artifacts to the image. FIG. 4C illustrates a longitudinal image of the calibration pad 10 showing the reference samples. The diagonal line and the thin vertical line are representations of the pointing device and are not artifacts in the image.

Calibration measurements are expressed in a regression equation of the form $y = I_o + S \times HU_s$. The slope, S, of the regression curves is related to the effective beam energy used to make the image. For each different KVps, filtration of the primary beam, and different patient sizes and compositions, the slope varies. The intercept, $I_o$, of the regression equation is a measure of the bias and is determined form the patient's own blood/muscle tissues in the hybrid calibration method. The slope, S, will vary with location in a given patient due to differing amounts and densities of tissue being present in the beam.

Voxels within the boundaries of the reference samples are automatically recorded and are then used to calculate a histogram. The histogram may be smoothed or a Gaussian curve in accordance with known methods. The ROI readings from several neighboring slices may be integrated for improved statistics. The ends of the histogram may be clipped to remove partial volume or blurred voxel readings from the margins of samples.

The calculated mode is next combined with the phantom regression equation to create the final hybrid calibration equation. The calibration equation is an expression of the form:

$$T_d = (HU_b - HU'_b) + S \times HU$$

In the foregoing expression, $T_d$ is the tissue density of the target tissue or organ to be analyzed. The tissue density $T_d$ may be expressed as corrected HU values or $T_d$ may be represented in tissue density units such as grams per cubic centimeter (g/cc). The parameter $HU_b$ is the previously determined or known CT number of representative blood/muscle, or other tissues. The parameter $HU'_b$ is the measured reference tissue density, which in this example may be the mode of the histogram of the heart and blood, the mode of fat or a calculated soft tissue representative (STR) calculated from the fat and muscle/blood of the patient. The parameter S is the slope of the regression equation measured from the calibration phantom samples. The parameter HU is the scanner CT number or may be a CT number measure of the target tissue to be analyzed. Note that the target tissue may be coronary calcifications, an organ, an unknown mass, or the edge of a target region or organ.

When the detail is imaged in, for example, a CT scanner (e.g., the CT scanner 14 of FIG. 1), the final image may have 12 or more bits of gray scale values. All of the gray scale values cannot be displayed at one time on a monitor, and further, the eye cannot see this many gray levels. The image is therefore displayed with windows (number of gray levels) and levels (the central gray level of the window). A variety of windows and levels are possible and can be based on the calibrated tissue readings.

The calcium reference samples 34 and 36 in the calibration pad 10 have a composition closely equivalent to calcifications within the patient since both are largely composed of calcium hydroxyapatite (CaHA). Any change in effective x-ray beam energy from scanner drifts, tube changes, different CT scanners, filtration and highly important, differences in patient compositions are largely corrected for by the calibration process which occurs on every CT image. Likewise the iodine reference sample 38 is closely representative of iodine contrast media injected into the blood vessels of the patient and blood perfusion into tissues.

Figure 5A:
Figure 5B:
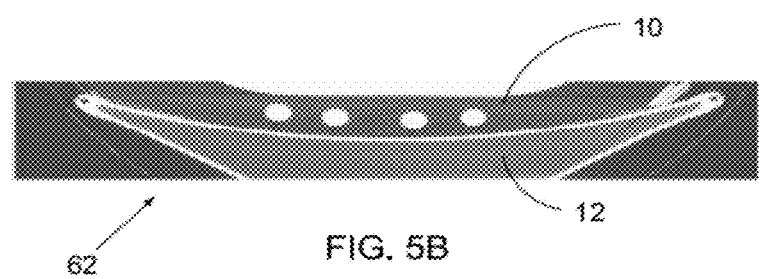

FIGS. 5A and 5B illustrate an axial CT image 60 of the abdominal region of a patient with the calibration pad 10 present under the patient. FIG. 5A shows the CT image at a customary window/level display setting. The display setting of window and level are representatively shown in calibrated units of mg per cubic centimeter in contrast to common displays with uncalibrated images in Hounsfield units (HU). FIG. 5B illustrates an insert 62 windowed to low level and increased window to show the position of the pad within the CT table 12. As illustrated in FIG. 5B, the improved calibration pad does not introduce artifacts in the image even at the low level and increased window settings chosen to demonstrate artifacts if they were present.

Figure 6A:
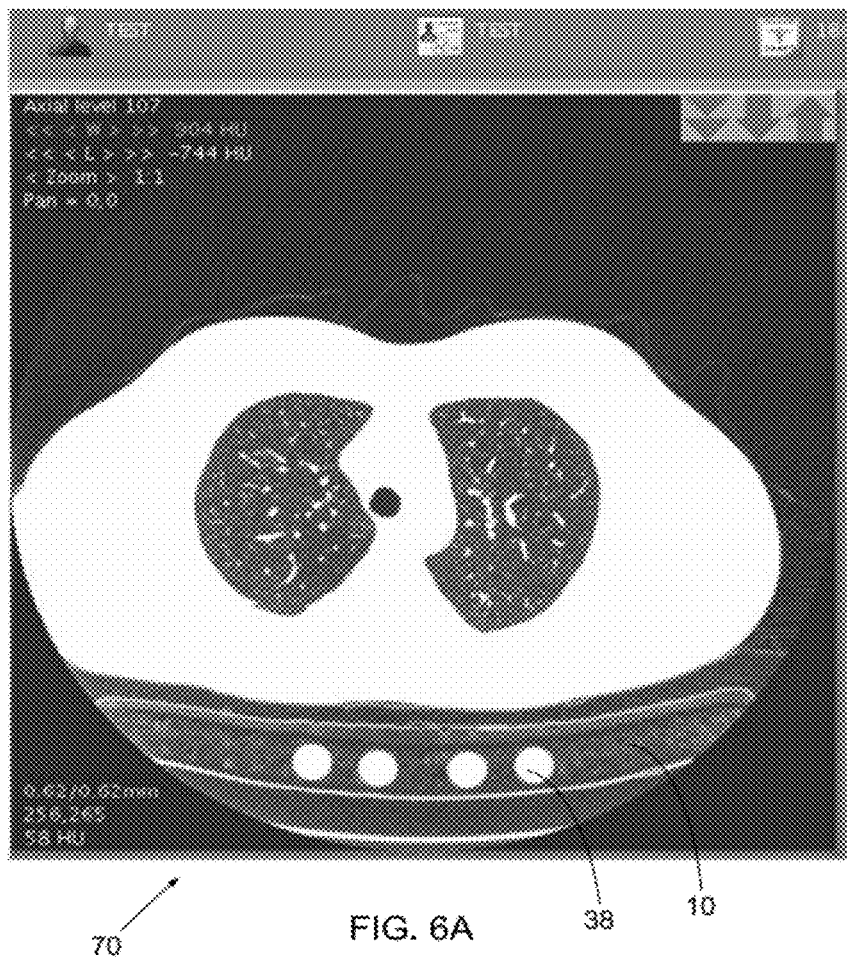
Figure 6B:
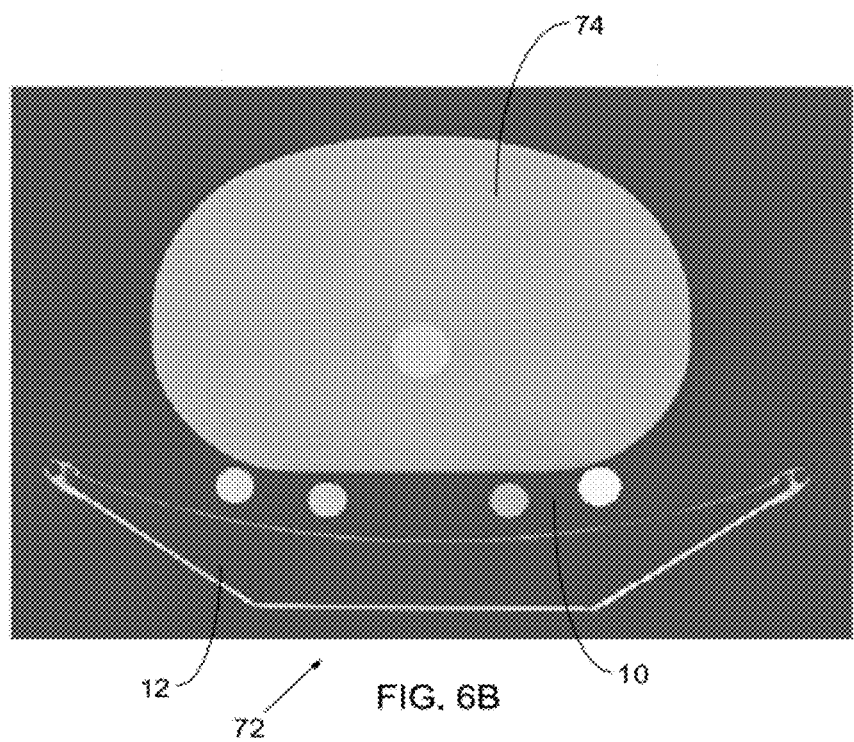
Figure 6C:
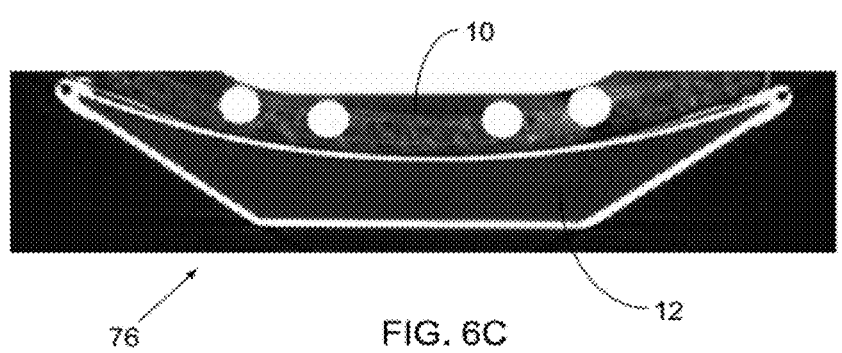

FIGS. 6A, 6B and 6C illustrate scans of the pad in one embodiment containing an iodine reference sample. FIG. 6A is an axial reconstructed CT image 70 of the chest region of a patient with the calibration pad 10 containing the iodine reference 38 with an NaI concentration of 2% by weight.

FIG. 6B is an axial image 72 of a simple QA test phantom 74 with the calibration pad 10.

FIG. 6C illustrates a windowed image 76 of the calibration pad 10 and the CT table 12, which shows the absence of artifacts with the iodine sample 38 at the lowered window level. The image display of FIG. 6C also shows the low density of the foam like surrounding material of the pad and the low density of the core of the CT table under the pad which in another embodiment contains the samples within the table structure.

Dual energy CT (DECT) used in angiography studies and with or without vascular calcifications suffers from imperfect subtractions and imperfect image reconstructions as discussed above. Computation methods to improve the separation of two targets or tissues are needed and are dependent on the specific attenuation of specific patients. The availability of both calcium and iodine references in DECT images with known properties allows corrections to be made for improvements. Dual energy imaging in other devices such as 3-D DXA, tomosynthesis, rotational x-ray systems, and the like, can be improved by like processing with known references present in the images.

Scattered radiation in newer MDCT scanners with 16 to 256 detector rows is a major image degradation factor. By design, the MDCT scanners image a much larger volume of tissue in each rotation resulting in greatly increased scatter.

Scatter removal methods including grids, and post processing methods are imperfect resulting in loss of image detail and quantitative accuracy of the post-processed image. The available of reference samples and test objects in each image along with the patients provides known references at locations which can be determined. Reconstructed images can be forward-projected for corrections and calibrations. The processing uses the known references as the gold standard for that image by processing until the desired image properties are achieved. The processed images can then be back-projected again following the corrections. Alternatively, image processing can be performed directly on each CT view angle to achieve corrections based on a set ideal of the known reference. Current scatter correction methods are arbitrary and based on the CT scanner and exposing parameters. Corrections made based on the specific patients anatomy and body composition can improve scatter correction methods.

Figure 7:
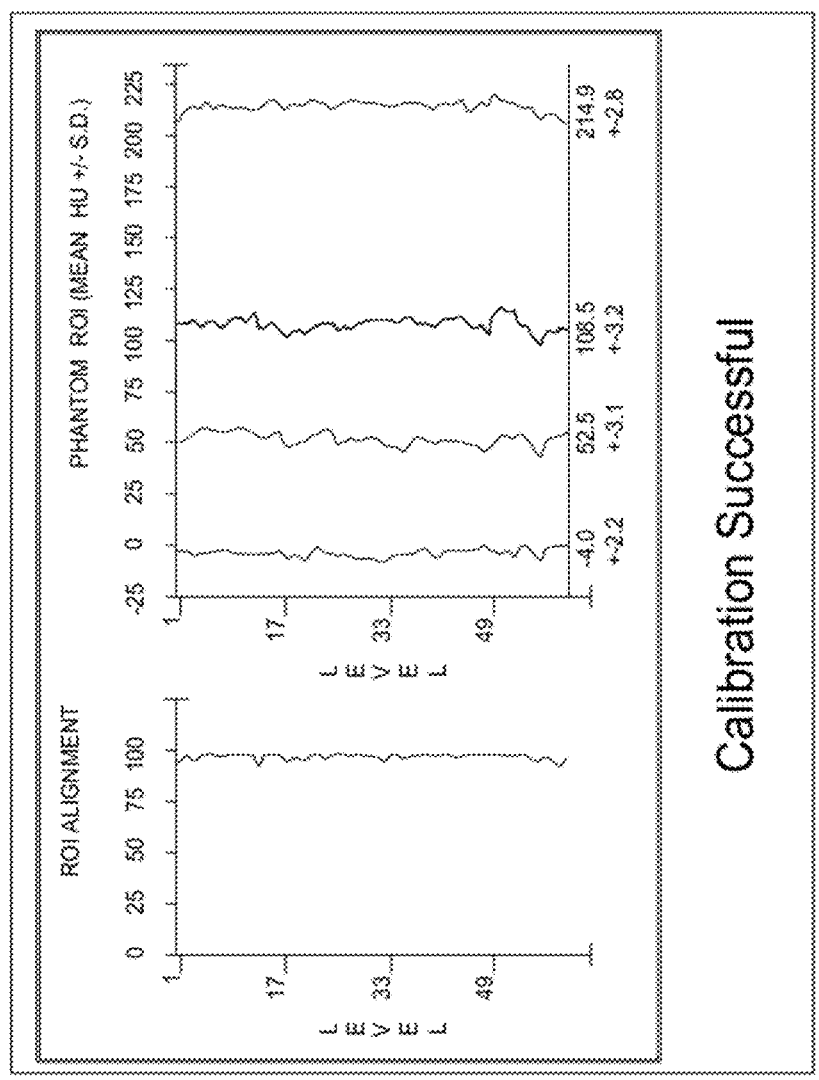
FIG. 7 illustrates an output graph from the automated software with measured calibration sample ROI readings along the Z-axis for representative samples, wherein the left side of FIG. 7 shows a figure-of-merit graph for measurement ROI centering on the small samples along the Z-axis.
Figure 8:
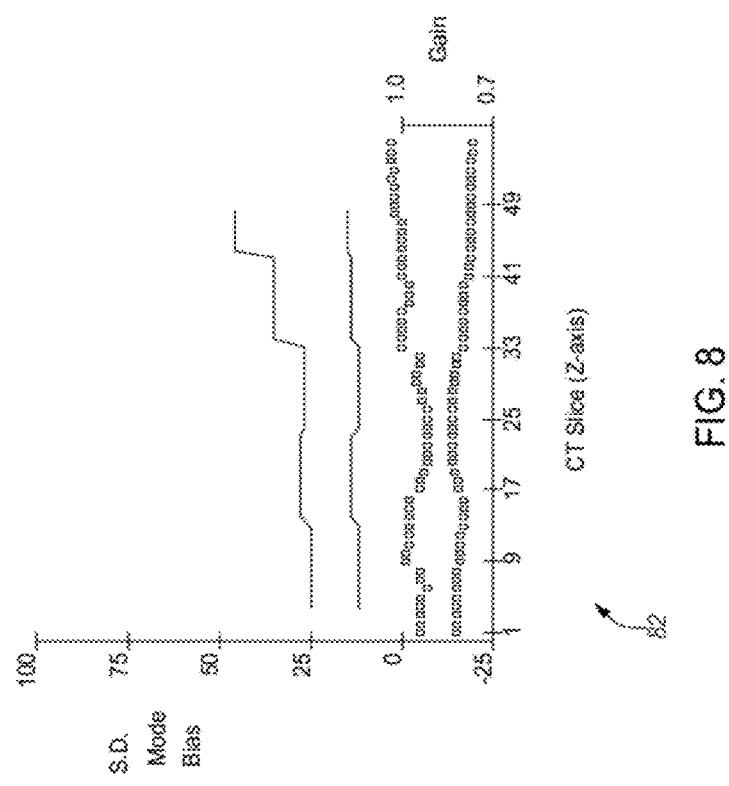
FIG. 8 illustrates an output graph from the automated software with hybrid calibration and z-axis image noise measurements, wherein the graph steps occur when a fixed Z-axis increment of n slices (in this example 16 slices) is integrated to reduce noise and to determine the hybrid calibration reading with improved statistical reliability.

FIG. 7 illustrates an exemplary display 80 wherein the right side of the display is an output graph of the data from the automated software disclosed herein with measured calibration sample ROI readings along the Z-axis for representative samples of the calibration pad 10. The left side of the display of FIG. 7 shows a figure-of-merit graph for measurement and verification of measurement ROI centering on the small samples and along the entire length of the Z-axis including the patients' anatomy FIG. 8 illustrates an exemplary display 82 of an output graph from the automated software disclosed herein with hybrid calibration and z-axis image noise measurements. The result steps in the graph occur when a fixed Z-axis increment of slices (16 slices) is integrated to determine the hybrid calibration reading with improved statistical reliability.

Figure 9:
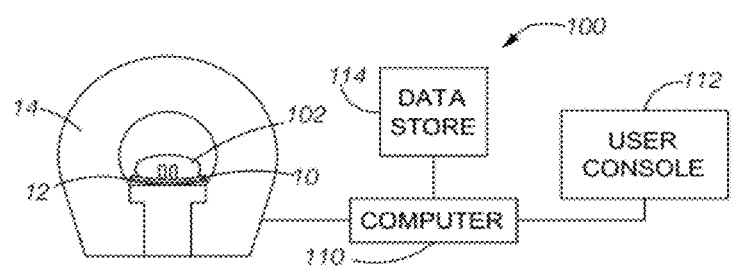
FIG. 9 illustrates an exemplary processing system for implementing the method in accordance with the present application.

FIG. 9 illustrates an exemplary system 100 that implements the method disclosed herein in combination with the calibration pad 10. In particular, a patient 102 is shown positioned on the calibration pad within the CT scanner 14. The measurements from the CT scanner 14 are electronically communicated to a data processing subsystem (computer) 110 that operates in accordance with the software method described below. The computer is coupled to a user console 112 (comprising, for example, a display device, one or more data entry devices and a cursor control devices) and to a storage unit 114. The console and the storage unit may be part of the computer or may be external components. The measurements may be communicated directed from the CT scanner to the computer or may be stored and then later communicated to the computer. Although shown as a separate unit, the computer may be included as part of the CT scanner.

FIG. 10 illustrates a flow chart 120 of exemplary steps used in the methods to detect the small samples, center ROI in each and extract measurements automatically. The method is performed on the measurements from the CT scanner in accordance with stored instructions retrieved and executed by the computer 110 (FIG. 9). The detection of the small samples in the image of the calibration pad 10 occurs totally automatically without operator interaction or supervision in accordance with innovative image processing techniques and algorithms. The algorithms use known circular shape, cross-sectional size, and approximately known locations of the samples within the support pad or table to identify likely candidates. The detection method checks for acceptable density ranges and sizes at multiple locations along the sample lengths and in likely locations. The search begins at the likely midpoint of the scan along the Z-axis region. If successful, second and third searches are used at ¼ and ¾ of the scan ranges, which sub-lengths are further sub-divided and in continuum to optimize the search time and location of the extended samples. When likely sample cross-sections are identified and located, feature extraction image processing techniques are next applied to locate and center ROIs within the samples repeatedly along the z-axis extent of the pad image. A preferred embodiment advantageously uses the methods as disclosed in FIG. 10. Typically a large number of Images are to be calibrated.

In a first step 130 of the flow chart 120 of FIG. 10, a prior method such as disclosed in U.S. Pat. No. 4,922,915 to Arnold, which is incorporated by reference herein, is used to determine a start y pixel of the image of a reference object in the calibration pad positioned under the subject. In a step 132, the y location is shifted up by a distance of n pixels from the y pixel start location to approximate the center of the known size of the reference inserts. Next, in a step 134, the standard deviations (stdev) are calculated for a search ROI of n×n pixels which is centered on this location. This measurement is repeated for 4 adjacent ROI locations.

In a step 136, a lowest standard deviation (stdev) is determined, and a new start location is determined and centered at the center pixel of the ROI with the lowest stdev. The stdev is determined for each of 4 new adjacent ROIs centered at the new start location. As illustrated in a step 140, the steps 132, 134 and 136 are repeated until no ROI position is found with a lower stdev than in the preceding iteration.

The center of the ROI determined in the step 140 is saved as an object center location (Lo) used for additional image processing. In a step 142, a new search ROI is located at Lo. The new search ROI has a radius equal to 4 times the object radius. In a step 144, edge detection is performed in the new search ROI. Then, in a step 146, the Hough Transform is applied with a diameter equal to the known object diameter. Following a first preprocessing step with an edge detection algorithm with constraints optimized to the expected shape and densities of the samples, candidate edges are applied to the Hough Transform to extract the desired feature of sample x-y Center-of-Area (CoA). Deviations from circular shaped edges are automatically excluded in preference for those with best fits. From the selected edge boundaries and satisfying sanity checks, the x, y, and z locations of the selected outlines are determined. A circular ROI of area smaller than the known sample is then centered at the CoA in a step 150. Preferably, the ROI has a radius of approximately 70% of the known object radius (e.g., 0.707 times the known object radius). A goodness-of-fit criteria is calculated based on the standard deviation of the pixel reading within the positioned ROI which serves to verify centering of the ROI at or near the center of the small samples. It is important that pixel readings at and near the edges of the samples are not employed in the final calibrations. The pixel values in the final ROI are recorded in a step 152. As illustrated by a step 154, the preceding steps of the method are repeated for each of the objects which may be present in each image. For example, in the illustrated embodiment of the calibration pad 10, the images of the 4 round samples are located and measured. As illustrated by a step 156, the method is repeated for each of N images which contain the reference objects. The software that implements the method thus records n ROI values per image times the number of images in a study.

As illustrated by a step 160, the pixel values may be summed in a certain number of the final ROIs of adjacent images to reduce noise effects due to the very small samples. Then, in a step 162, a histogram of the pixel values of the sum of n adjacent ROIs of each object is then calculated. After completing the foregoing steps, an additional step of fitting a Gaussian curve to the histogram distribution of pixel readings may be implemented. The two tails of the histogram are preferably clipped to a level of approximately 10%. The final sample ROI reading is the average of the pixel intensities within the so positioned and processed ROI. The mean and stdev of the pixel values are calculated from the sum of each of the ROIs of each object in a step 164. These values are the sample readings used for calibration or correction. The values are determined automatically in background mode without operator interaction. In a step 166, the values are provided as the return values from the method, and the method then stops.

Figure 10A:
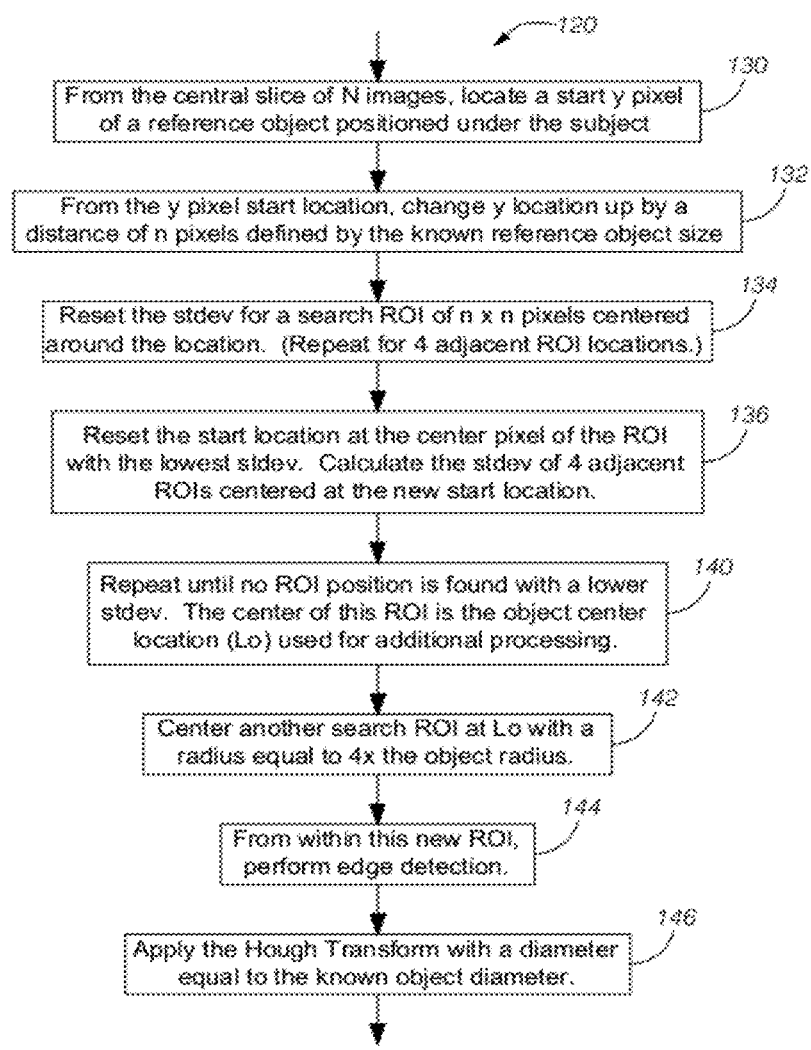
FIGS. 10A and 10B illustrated a flow chart of the automated phantom finder software used with the new calibration device with smaller area and lengthy samples.
Figure 10B:
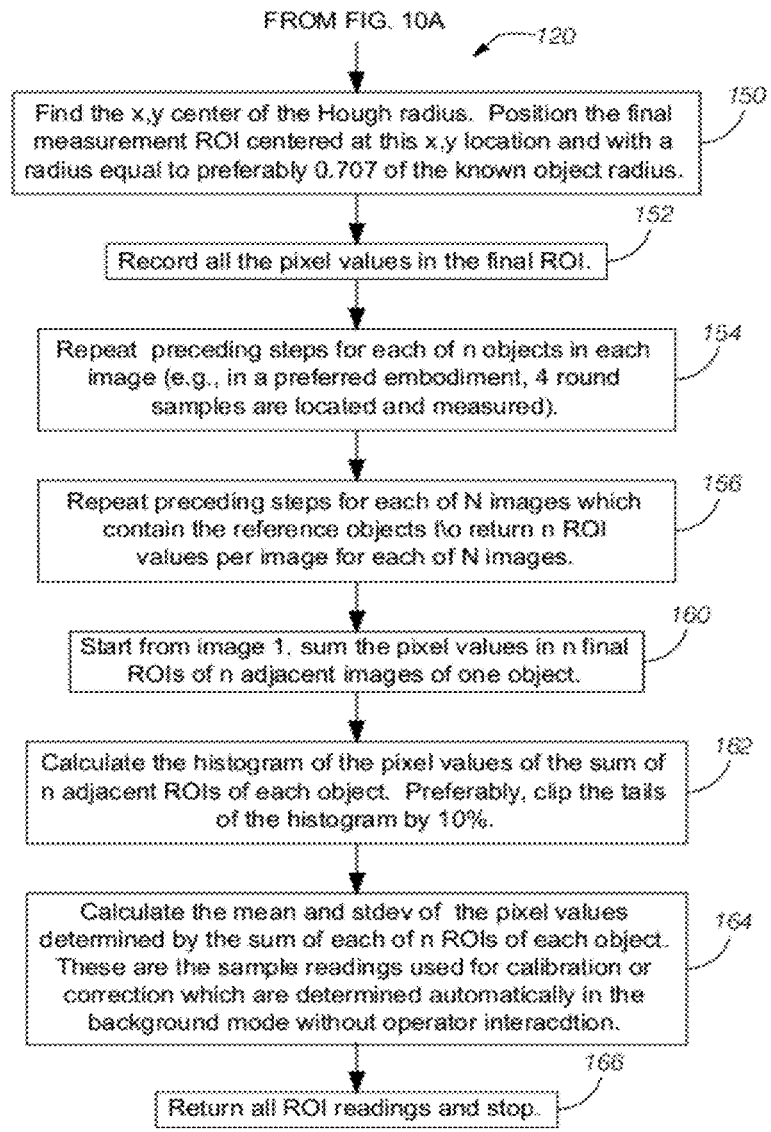

FIG. 11 illustrates an exemplary display 180 on an output screen from the automated software that implements the method of FIGS. 10A and 10B. As illustrated in the lower left portion of the display in FIG. 11, icons for six calibrated application programs are available for selection by a user. Selecting the upper left icon 182 initiates an automated coronary calcium scoring program. Selecting the upper middle icon 184 initiates a trace coronary calcium scoring program. Selecting the upper right icon 186 initiates an aortic calcium scoring program. Selecting the lower left icon 188 initiates a spinal bone density program. Selecting the lower middle icon 190 initiates a hip bone density program. Selecting the lower right icon 192 initiates a quality control program for use with the simple QA test phantom lying on the calibration pad. The upper right screen shows the sample readings after corrections and processing as described above in FIGS. 10A and 10B. The Figure-of-Merit measurement for ROI centering is shown at the left side of the window. The screen shown in FIG. 11 is exemplary of the method implemented by the software program, which use icons instead of text throughout the program so that the system is easier to use by practitioners in any native language.

One skilled in art will appreciate that the foregoing embodiments are illustrative of the present invention. The present invention can be advantageously incorporated into alternative embodiments and a variety of imaging devices which produce axial images or volumetric scans while remaining within the spirit and scope of the present invention, as defined by the appended claims.

What is claimed is:

1. A method for calibrating and correcting images acquired with a three-dimensional imaging device by simultaneously scanning a subject and a reference pad with at least one calibration insert of known physical properties representative of tissues, injected contrast, or materials in the body of a subject, scanning the body of the subject and the reference pad under similar imaging conditions, the method including a computer software program for locating the at least one calibration insert and for recording readings, the method further comprising:

positioning the reference pad and at least one calibration insert on a subject support surface, the reference pad extending for substantially the full length of the subject's torso without discontinuity, the reference pad supporting the full length of the subject's torso, the reference pad being independent from but supported by the table of the imaging device, the at least one calibration insert being encased in foam and enclosed within the reference pad, wherein the at least one calibration insert comprises an aluminum wire extending substantially the length of the subject's torso, the aluminum wire having a diameter less than a point spread function (PSF) of the imaging device;

automatically locating the at least one calibration insert at multiple locations and automatically recording readings with a computer; and modifying the images based on the readings.

2. The method of claim 1, wherein the subject support surface is a top surface of a table of the imaging device.

3. The method of claim 1, wherein the readings comprise parameters determined from the recorded CT attenuation values of voxels representing regions of the at least one calibration insert with known properties.

4. The method of claim 1, wherein the at least one calibration insert has a size and mass such that the calibration insert does not create image artifacts when imaged with the subject.

5. The method of claim 1, wherein the imaging device is a three-dimensional, dual-energy X-ray absorptometry (3 D DXA) device.

6. A method for calibrating and correcting images acquired with a three-dimensional imaging device by simultaneously scanning a subject and a reference pad with at least one calibration insert of known physical properties representative of tissues, injected contrast, or materials in the body of a subject, scanning the body of the subject and the reference pad under similar imaging conditions, the method including a computer software program for locating the at least one calibration insert and for recording readings, the method further comprising:

positioning the reference pad and at least one calibration insert on a subject support surface, the reference pad extending for substantially the full length of the subject's torso without discontinuity, the reference pad supporting the full length of the subject's torso, the reference pad being independent from but supported by the table of the imaging device, the at least one calibration insert being encased in foam and enclosed within the reference pad, wherein the at least one calibration insert comprises microspheres of calcium hydroxyapatite or aluminum located at repeated positions along substantially the entire length of the reference pad, the microspheres having diameters less than a point spread function (PSF) of the imaging device;

automatically locating the at least one calibration insert at multiple locations and automatically recording readings with a computer; and modifying the images based on the readings.

7. The method of claim 6, wherein the subject support surface is a top surface of a table of the imaging device.

8. The method of claim 6, wherein the readings comprise parameters determined from the recorded CT attenuation values of voxels representing regions of the at least one calibration insert with known properties.

9. The method of claim 6, wherein the at least one calibration insert has a size and mass such that the calibration insert does not create image artifacts when imaged with the subject.

10. The method of claim 6, wherein the imaging device is a three-dimensional, dual-energy X-ray absorptometry (3 D DXA) device.

11. A method to identify and locate and measure the attenuation properties of known references scanned simultaneously with the subject in a three-dimensional imaging apparatus, said references further having known properties, the method comprising:

encasing a plurality of references in a foam support structure, each of the references having a physical size in at least one dimension that is less than a point spread function (PSF) of the imaging apparatus, the references distributed at selected locations along a length of the foam support structure greater than the length of the torso of a subject;

positioning the subject on the foam support structure;

imaging the subject and the references using the three-dimensional imaging apparatus; and automatically searching locating and analyzing the references to modify an image of the subject.

12. The method of claim 11, wherein locating and analyzing the references is performed without operator interactions.

13. The system of claim 11, wherein the selected locations are repeated fixed locations along the length of the foam support structure.

14. The system of claim 11, wherein the references comprise microspheres of calcium hydroxyapatite or aluminum.

15. The system of claim 11, wherein the references are metallic.

* * * * *